(12) United States Patent
Wang et al.

(10) Patent No.: US 9,395,349 B2
(45) Date of Patent: Jul. 19, 2016

(54) ELECTRODE STRUCTURE AND APPARATUS FOR USE IN MEASURING OIL-WATER CONSTITUENTS

(75) Inventors: Qiming Wang, Weihai (CN); Guoyong Cheng, Weihai (CN)

(73) Assignee: WEIHAI HAIHER TECHNOLOGY CO., Weihai, Shandong (CN)

( * ) Notice: Subject to any disclaimer, the term of this patent is extended or adjusted under 35 U.S.C. 154(b) by 313 days.

(21) Appl. No.: 14/008,407

(22) PCT Filed: Jan. 9, 2012

(86) PCT No.: PCT/CN2012/070125
§ 371 (c)(1),
(2), (4) Date: Sep. 27, 2013

(87) PCT Pub. No.: WO2012/129972
PCT Pub. Date: Oct. 4, 2012

(65) Prior Publication Data
US 2014/0013830 A1 Jan. 16, 2014

(30) Foreign Application Priority Data

| Mar. 28, 2011 | (CN) | .......................... 2011 1 0087369 |
| Jun. 2, 2011 | (CN) | .......................... 2011 1 0158124 |
| Jun. 2, 2011 | (CN) | ...................... 2011 2 0198393 U |

(51) Int. Cl.
*G01N 33/28* (2006.01)
*G01N 27/22* (2006.01)

(52) U.S. Cl.
CPC .......... *G01N 33/2847* (2013.01); *G01N 27/226* (2013.01)

(58) Field of Classification Search
CPC ........... B01D 17/0214; G01N 33/1833; G01N 33/2847; G01N 27/226
USPC ......................... 324/640, 664–670; 73/304 C
See application file for complete search history.

(56) References Cited

U.S. PATENT DOCUMENTS

| 3,010,320 | A | * | 11/1961 | Sollecito | ............... | G01F 23/263 |
| | | | | | | 361/284 |
| 3,437,924 | A | * | 4/1969 | Tocanne | ............... | E21B 47/102 |
| | | | | | | 324/324 |

(Continued)

FOREIGN PATENT DOCUMENTS

| CN | 2248874 Y | 3/1997 |
| CN | 2315543 Y | 4/1999 |

(Continued)

OTHER PUBLICATIONS

First Chinese Office Action regarding Application No. 201280001767.5, dated Dec. 25, 2013. Partial translation provided by Unitalen Attorneys at Law.

(Continued)

*Primary Examiner* — Peter Macchiarolo
*Assistant Examiner* — Nathaniel Kolb
(74) *Attorney, Agent, or Firm* — U. S. Fairsky LLP; Yue Xu

(57) ABSTRACT

An electrode structure and apparatus for use in measuring oil-water constituents. The electrode structure comprises a first electrode (1) and a second electrode (2). The first electrode (1) has wrapped on the exterior thereof an insulating layer (104). The first electrode (1) and the second electrode (2) are fixed and insulatively connected via a supporting connector body (3). The first electrode (1) comprises multiple tubular conductive segment sub-electrodes (101) arranged along a first direction. Every two adjacent segment sub-electrodes (101) have formed therebetween a first gap. The second electrode (2) is arranged around the first electrode (1), and both are electrically connected to a signal and data processing unit (5).

15 Claims, 6 Drawing Sheets

(56) References Cited

U.S. PATENT DOCUMENTS

| | | | |
|---|---|---|---|
| 4,170,135 A * | 10/1979 | Booman | G01F 23/284 |
| | | | 73/290 R |
| 4,429,581 A | 2/1984 | Furmaga et al. | |
| 4,543,823 A * | 10/1985 | Nagy | G01F 23/284 |
| | | | 324/642 |
| 6,136,174 A | 10/2000 | Berry et al. | |
| 6,420,882 B1 * | 7/2002 | Engebretsen | G01F 23/266 |
| | | | 324/667 |
| 2002/0070734 A1 * | 6/2002 | Engebretsen | G01F 23/266 |
| | | | 324/667 |

FOREIGN PATENT DOCUMENTS

| | | | | | |
|---|---|---|---|---|---|
| CN | 1228530 | A | 9/1999 | | |
| CN | 2354136 | Y | 12/1999 | | |
| CN | 1375435 | A | 10/2002 | | |
| CN | 1207540 | C | 6/2005 | | |
| CN | 1769375 | A | 5/2006 | | |
| CN | 2778391 | Y | 5/2006 | | |
| CN | 1908595 | A | 2/2007 | | |
| CN | 1959397 | A | 5/2007 | | |
| CN | 101042304 | A | 9/2007 | | |
| CN | 200982955 | Y | 11/2007 | | |
| CN | 201063029 | Y | 5/2008 | | |
| CN | 201092853 | Y | 7/2008 | | |
| CN | 101408444 | A | 4/2009 | | |
| CN | 101532863 | A | 9/2009 | | |
| CN | 101737041 | A | 6/2010 | | |
| CN | 202126424 | U | 1/2012 | | |
| GB | 1378260 | A | * 12/1974 | | B01D 17/0214 |
| RU | 2037151 | C1 | 6/1995 | | |

OTHER PUBLICATIONS

International Search Report (in Chinese with English translation) and Written Opinion (in Chinese) for PCT/CN2012/070125, mailed Apr. 12, 2012; ISA/CN.

First Chinese Office Action regarding Application No. 201280001771.1, issued Sep. 4, 2013. Partial translation provided by Unitalen Attorneys at Law.

* cited by examiner

ELECTRODE STRUCTURE AND APPARATUS FOR USE IN MEASURING OIL-WATER CONSTITUENTS

CROSS-REFERENCE TO RELATED APPLICATIONS

This application is the US national phase of International Application No. PCT/CN2012070125 filed on Jan. 9, 2012, which claims the benefit of priority to Chinese patent application No. 201120198393.3 titled "INTEGRATED APPARATUS FOR MEASURING WATER CONTENT", filed with the Chinese State Intellectual Property Office on Jun. 2, 2011; the benefit of priority to Chinese patent application No. 201110158124.9 titled "INTEGRATED APPARATUS FOR MEASURING WATER CONTENT", filed with the Chinese State Intellectual Property Office on Jun. 2, 2011; and the benefit of priority to Chinese patent application No. 201110087369.7 titled "METERING METHOD AND APPARATUS FOR OIL CONTENT OF PRODUCED LIQUID OF OIL WELL", filed with the Chinese State Intellectual Property Office on Mar. 28, 2011. The entire disclosures thereof are incorporated herein by reference.

FIELD OF THE INVENTION

The present invention relates to an apparatus for measuring net content of a single-phase medium within a multiphase mixed storage medium tank containing water, in particular relates to an integrated apparatus for measuring water content, the apparatus is particular suitable for precisely measuring the net content of the crude oil within a crude oil tank containing a oil-water emulsion layer in the petrochemical industry.

BACKGROUND OF THE INVENTION

In industrial application, it is common that a variety of organic media and water are mixed in a container. Therefore, it is required to measure the net content of the water or organic medium therein. In the petrochemical industry, a typical requirement is used to precisely measure the net content of the crude oil within a crude oil tank containing an oil-water emulsion layer. However, since the medium within the crude oil tank is distributed unevenly, there is not yet a mature technology meeting the above requirement now.

In the related prior art, the patent No. 02110211.2, entitled "multiphase material level sensor", previously proposed by the inventor of the present application provides a level measuring apparatus capable of qualitatively measuring the oil-water distribution in a crude oil tank. According to the technical solution, it is provided a measuring sensor, which is wrapped by an insulating layer and composed of multiple segment electrodes in the vertical direction. Segment electrodes composing the measuring sensor are independent of each other. A capacitive or impedance sensor is formed by each of the segment electrodes and the wall of the tank, which is referred to as a segment sensor. The medium between a segment electrode and the tank is function as electrolyte of the corresponding segment sensor. Output signals of each of the segment sensors are transported to a signal and data processing unit that is located on the outside of the tank through the respective cable directly or through a data bus after an A/D conversion. The signal and data processing unit determines the property of the medium in the tank according to the property and amplitude of the output signal of the segment sensor corresponding to the medium, thereby obtaining the general distribution of the medium within the tank in the vertical direction.

The problems of the existing technical solutions are as follows, firstly, the apparatus that is provided in the tank meeting the requirement of production or the like, may significantly affect the measuring signal of the segment sensor, thereby affecting the measuring of the medium distribution within the tank by the signal and data processing unit. Secondly, since the distance from the outer surface of a segment electrode to the wall of the tank is far more than the height of the segment electrode in the vertical direction, besides the horizontal medium layer on which the segment sensor is located, horizontal medium layers in a certain distance above and below the horizontal medium layer may affect output signals of the segment sensor. Because the property of each horizontal medium layer within the tank is uncertain, the effect on output signals of the horizontal medium layer generated by the horizontal medium layers above and below the horizontal medium layer is uncertain. In this way, according to the existing technical solution, the distribution in the vertical direction of the multiphase medium including water in a tank can be measured approximately, but the composition, such as the water content, of the medium layer on which the segment sensor is located, can not be measured accurately.

SUMMARY OF THE INVENTION

The problem to be solved by the present invention is how to overcome defects of the existing technology. According to the present invention, it is provided an integrated apparatus for measuring water content, of which the structure is reasonable, the operation is convenient, the measurement is accuracy and reliable. The accurate measurement of the composition of each horizontal layer of multiphase medium within a container in turn can be achieved by employing the integrated apparatus for measuring water content.

The technical solutions of the present invention solving the above technical problem are as follows: an electrode structure for measuring water content, including a first electrode and a second electrode, herein, an insulating layer is wrapped around the first electrode, and the first electrode and the second electrode are fixed and connected to each other via a supporting and connecting body insulatively, herein:

the first electrode includes a plurality of tubular conductive segment electrodes arranged along a first direction, every two adjacent segment electrodes are insulated from each other, a first space is formed between the two adjacent segment electrodes, the two adjacent segment electrodes are operately electrically connected to a signal and data processing unit respectively, the second electrode is arranged around the first electrode and extends along the first direction, and is operately electrically connected to the signal and data processing unit;

a second space is formed between the first electrode and the second electrode in a second direction perpendicular to the first direction.

According to another embodiment of the present invention, there is provided an integrated apparatus for measuring water content, including:

a container, arranged vertically for accommodating a multiphase medium liquid; and an electrode structure as described above, which is arranged in a tank, and the first direction of the electrode structure is a vertical direction.

Preferably, the length of the second space is smaller than the height of the segment electrode of the first electrode.

The advantages of the technical solution of the present invention are as follows:

in the electrode structure, firstly, according to the present invention, the effect on the electrical parameter of each medium layer generated by a irregular container and an unknown apparatus in the container can be eliminated, such that measuring results are no longer influenced by the internal structure of a the container. Secondly, the effect on the electrical parameter of the measured medium layer generated by the adjacent layers can be eliminated approximately according to the dimensional relationship between the height of the segment electrode and the length of the second space described by the present invention, so that the composition parameter of the medium in the measured medium layer can correspond to the electrical parameter of the corresponding segment sensor, thereby accurately measuring the water content of each horizontal medium layer. The number of the blind spots of each segment electrode is reduced based on the configuration of the insulation distance between the adjacent segment electrodes.

Thereby, according to the present invention, in the vertical direction, multiple water content measuring probes with a small size are combined together in order, these water content measuring probes are adjacent to each other, and there is almost no measuring blind spot. Each of the water content measuring probe can accurately measure the water content of the horizontal medium layer on which the water content measuring probe is located, this is impossible in the prior art. After the integrated apparatus for measuring water content is installed, the height of the position of each of the water content measuring probes and the thickness of the measured horizontal medium layer are determined, combining with the internal lateral dimensions of the container, the net content of single-phase medium within the multiphase mixed storage medium tank containing water can be measured through combining with internal lateral dimensions of the container. Meanwhile, since the first electrode is provided with an external insulating layer, the failure of the water content measuring probe caused by the conductivity of the water is eliminated; the influence on medium hanging is minimized by the second electrode which is formed by several branch conductive, tubular or rod-shaped electrodes in parallel.

The apparatus of the present invention has the following features: a reasonable structure, convenient operation, accuracy and reliable measuring result, accurate measurement of the compositions of each horizontal layer of multiphase medium within a container. And the apparatus is particularly suitable for precisely measuring the net content of the crude oil within a crude oil tank containing a water emulsion layer in the petrochemical industry.

BRIEF DESCRIPTION OF THE DRAWINGS

The further description of the present invention will be made with reference to the attached drawings below.

Figure 1:
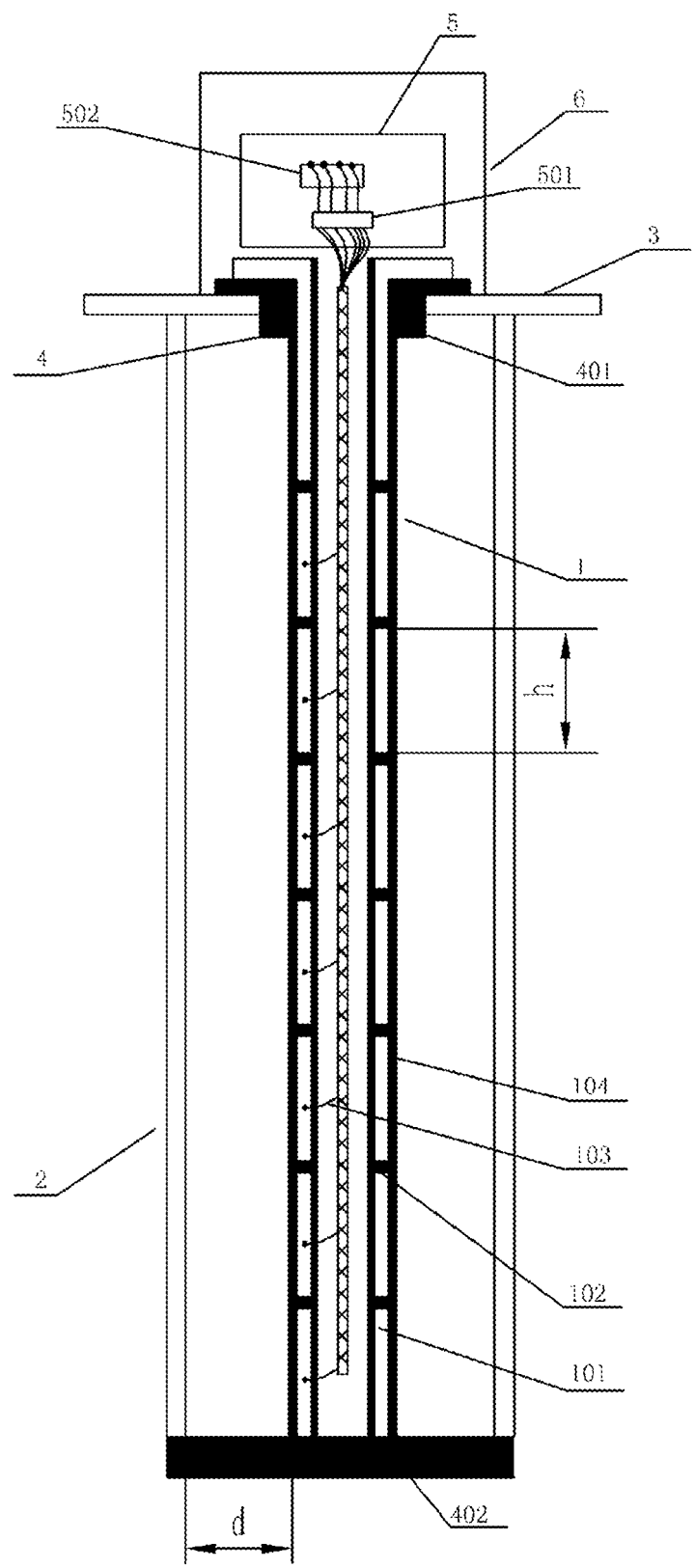
FIG. 1 is a schematic view of a composition structure according to the present invention.

Numbers in the drawings are as follows: 1. first electrode, 2. second electrode, 3. supporting and connecting body, 4. isolation insulating part, 5. signal and data processing unit, 6. electrical protective shell, 101. segment electrode, 102. insulated fastener, 103. segment electrode lead, 104. insulating layer, 105. segment signal measuring circuit, 106. data transfer bus, 201. second electrode lead, 202. connector, 401. isolation insulating head, 402. isolation insulating plug, 501. electronic switch, 502. common segment signal measurement circuit. G1. separation tank or container, G101. water collection bin at the bottom portion of the separation tank, G102. oil collection bin in the middle portion of the separation tank, G103. gas collection bin on the upper portion of the separation tank; G2. produce liquid of oil well input pipeline, G201. manual liquid inlet valve, G202. electric liquid inlet valve, G3. liquid output pipeline, G301. manual liquid drain valve, G302. electric liquid drain valve, G4. gas output pipeline, G401. manual exhaust valve, G402. electric exhaust valve, G5. liquid level indicator, G6. oil-water composition measuring apparatus, 601\602\603 . . . oil-water composition measuring apparatus probe, G7. data processing and control unit.

DETAILED DESCRIPTION OF THE EMBODIMENTS

According to an embodiment of the present invention, there is provided an integrated apparatus for measuring water content including a signal and data processing unit, a supporting and connecting body, and a sensor extending into a container to contact to multiphase medium. Herein, the sensor includes a first electrode and a second electrode, the first electrode and the second electrode are fixed and connected to the supporting and connecting body respectively; the first electrode is composed of a group of tubular conductive segment electrodes in the vertical direction, and the segment electrodes are fixed and insulated to each other via an insulating material, and are electrically connected to the signal and data processing unit through a lead located inside the segment electrode; an insulating layer is uniformly wrapped on the first electrode; and the first electrode is a integrated rigid composite electrode.

The second electrode is located along with the first electrode in the vertical direction and is electrically connected to the signal and data processing unit. The first electrode and the second electrode are parallel to each other in the vertical direction. The first electrode and the second electrode are spaced from and insulated to each other via an isolation insulating part in a second direction, such as the horizontal direction. The space between the second electrode and the first electrode is a measuring space of the sensor.

The second electrode according to the present invention is formed by several conductive tubular or rod-shaped electrodes connected in parallel. The second electrode formed by several conductive, tubular or rod-shaped electrodes connected in parallel has the following advantages: it is easy to process the surface of the tubular or rod-shaped electrode to be more smooth; and in the vertical direction of the measuring area, there is no protruding point which can block the movement of medium, thereby minimizing influence of hanging; it is significant in measurement of crude oil emulsion with a higher viscosity.

The second electrode according to the present invention may also have a conductive cylindrical structure. The lateral surface of the cylindrical structure is provided with holes which are distributed uniformly along the horizontal direction and the vertical direction, so as to facilitate the medium to get into and out of the measuring space.

In the present invention, for the height of the segment electrode composing the first electrode in the vertical direction, a corresponding size can be selected depending on different requirements on measurement accuracy in application. In principle, various segment electrodes may have different heights; however, in a preferred solution the same height is employed to simplify data processing.

In the case that the measuring space is not partitioned by the hanging, the distance between the first electrode and the second electrode is smaller than the height of the segment electrode in the vertical direction, so as to reduce the effect on measured medium layer generated by the adjacent medium layers.

An uniform insulating layer which is wrapped on the whole first electrode to isolate the first electrode from the measured medium, is composed of a film-shaped insulating material or an insulating material having a certain thickness and a relative higher dielectric coefficient, such as the resin doping a high dielectric coefficient material, plastic, rubber etc, so as to reduce the effect of a parasitic parameter on the measuring signal of the segment electrode.

In the technical solution according to the present invention, the segment sensors may share one or more segment signal measuring circuits. The segment signal measuring circuit is electrically connected to the signal and data processing unit, and is electrically connected to the segment electrode via an electronic switch. Each of the segment sensors may configure its own segment signal measuring circuit, and is electrically connected to the signal and data processing unit via a serial or parallel data bus after an A/D conversion.

As shown in FIG. 1, the integrated apparatus for measuring water content according to the present invention is used to measure the net content of single-phase medium within a medium tank in which multiphase medium is stored. The apparatus of the embodiment is used to measure water content of each horizontal medium layer within a medium tank in which multiphase medium is stored, therefore it is also referred to as a water content analyzer array. The water content analyzer array includes a signal and data processing unit 5, a supporting and connecting body 3, a sensor extending into a container and contacting to the multiphase medium, an isolation insulating part 4, and an electrical protective shell 6 etc. The sensor is composed of a first electrode 1 and a second electrode 2 which are parallel to each other in the vertical direction and are spaced from and insulated to each other in the horizontal direction. Herein, the first electrode 1 is composed of a group of tubular conductive segment electrodes 101 in the vertical direction, and the tubular conductive segment electrodes are independent of each other. The segment electrodes 101 are fixed and insulated to each other via an insulated fastener 102. The conductive outer surfaces of the segment electrodes 101 have a same transverse shape and size. The segment electrodes 101 are electrically connected to a signal and data processing unit 5 via a segment electrode leads 103 located inside the segment electrodes 101.

An uniform insulating layer 104 is wrapped on the whole first electrode 1 for isolating the segment electrodes 101 from the measured medium, without causing distortion of each segment electrode measuring signal.

The second electrode 2 is provided along with the first electrode 1 in the vertical direction. The space between the first electrode 1 and the second electrode 2, where the medium can freely get into and out of is function as the measuring space of the sensor. At a conductive side of the second electrode 2 that is face to the first electrode 1, the second electrode 2 has a same transverse structure and the uniform size at different heights. The second electrode 2 is provided with a passage which allows the medium to get into and out of the measuring space, and is generally electrically connected to the signal and data processing unit 5.

In the integrated apparatus for measuring water content according to the present invention, in the horizontal direction, the first electrode 1 is partially or completely surrounded by the second electrode 2; in the vertical direction, the first electrode 1 and the second electrode 2 are parallel to each other. The first electrode 1 and the second electrode 2 are fixed to and insulated from each other via an isolation insulating part 4 to form a detecting electrode of the sensor. That is, upper ends of the first electrode 1 and the second electrode 2 are fixed to and insulated from each other via an isolation insulating head 401, and lower ends of the first electrode 1 and the second electrode 2 are fixed to and insulated from each other via an isolation insulating plug 402.

The signal and data processing unit 5, the detecting electrode of the sensor and the electrical protective shell 6 and the like are connected together via the supporting and connecting body 3.

The multiphase mixed medium in a steady or balance state in the container is distributed in a demixed state, which is the premise condition that a technical solution proposed by the present invention is valid. A segment sensor or so-called water content measuring probe is composed of a segment electrode 101 located on the first electrode 1 and a portion of the first electrode 2 that is corresponds to the segment electrode. The electric signals, such as capacitance, impedance and the like, which are measured in such a manner that each segment sensor is cooperated with the respective segment signal measuring circuit 105, have different properties and values. The signal and data processing unit 5 determines the property of a medium layer according to the difference between electric signals sent from each of the segment sub-electrodes 101, and further obtains water content of a medium layer. Thus, it is required that the relevance between the signal of the segment sensor and the medium layer on which the segment sensor is located is as great as possible, while the relevance between the signal of the segment sensor and the adjacent medium lay is as small as possible. As shown in FIG. 1, after demonstrating, the relevance depends on the ratio of the minimum distance d between the first electrode 1 and the second electrode 2 to the vertical height h of the segment electrode 101, which is d/h for short. The higher the ratio of d to h is, the greater the effect on the signal of the segment sensor generated by the adjacent medium layer is, or reversely, the lower the ratio of d to h is, the less the effect on the signal of the segment sensor generated by the adjacent medium layer is. As demonstrated by a number of experiments, on account of the hanging between the first electrode 1 and the second electrode 2, the minimum distance d between the two electrodes is not allowed to be too small. In general, the distance between the first electrode and the second electrode is smaller than the height of the segment electrode in the vertical direction h. Preferably, the vertical height of the segment electrode ranges from 10 mm to 400 mm, and the minimum distance between the two electrodes ranges from 5 mm to 300 mm.

The space between the adjacent segment electrodes may be set to be 0.3 mm, and the maximum value of the space is less than the height of segment electrode.

For the height of the segment electrode 101 composing the first electrode in the vertical direction, different size can be selected depending on different requirements on application and measurement accuracy. In principle, the segment electrodes 101 may have different height, but in a preferable solution, the segment electrodes 101 have a same height to simplify data processing.

In a technical solution according to the present invention, it is provided an outer insulating layer 104 uniformly wrapped on the first electrode 1 to insulate the first electrode 1 from the measured medium which may be conductive, and reduce the process complexity of sensor assembling. Its influence on electric is equivalent to connecting a parasitic capacitive impedance element with the measured medium in series. In accordance with principles of electronics, in the case that the parasitic capacitance and the capacitive impedance of the measured medium are connected in parallel, the one with low impedance in the dominant position. In general, since the relative dielectric coefficient of the measured medium containing water is relatively great and is generally more than 3, compared with the parasitic capacitance, the capacitive impedance of the measured medium is relatively great. In order to reduce the influence of the parasitic capacitive impedance, it is required that the thickness of the outer insulating layer 104 is as thin as possible, for example, the thickness is less than 1.5 mm. Alternatively, although the thickness of the outer insulating layer 104 is great, the relative dielectric coefficient of insulating material is relatively great, such as the rubber, epoxy resin doping barium titanate and plastic etc, the relative dielectric coefficient of which is more than 3, thus increasing the capacitive impedance of the outer insulating layer as much as possible, and significantly minimizing the effect of the parasitic impedance. In accordance with specific conditions, it is possible to use the material the dielectric coefficient of which is less than 3. For example, in one embodiment, PTFE the dielectric coefficient of which is 2 is used.

The outer insulating layer may be provided in such a way that a layer of uniform insulating material is completely coated on the surface of the first electrode 1 through the spraying or injection moulding. Also, an insulated pipe which is distributed uniformly and matches well with the first electrode can also be prefabricated, and the insulated pipe is sleeved on the first electrode, in particular, it is necessary sealing measurement must be taken at the opening of the pipe.

In an embodiment of the present invention, a fluorine plastic film with the thickness of 0.3 mm and the relative dielectric coefficient that is not greater than 3 is used as the external insulating layer 104, and the external insulating layer tightly sticks to the outside of the first electrode by injection moulding.

In another embodiment of the present invention, a ceramic pipe with the thickness of 2.5 mm and the relative dielectric coefficient that is up to 30 is used as the external insulating layer 104, and is tightly sleeved on the outside of the first electrode, with the opening of the pipe being sealed by sealant.

The thickness of the insulating may depend on the material of the insulating film. For example, in an embodiment, the thickness of the insulating film is 3 mm.

The external insulating layer 104 of the present application may be a rubber tube or a plastic tube, and the outer insulating layer 104 is tightly sleeved on the outside of the first electrode.

Figure 2:
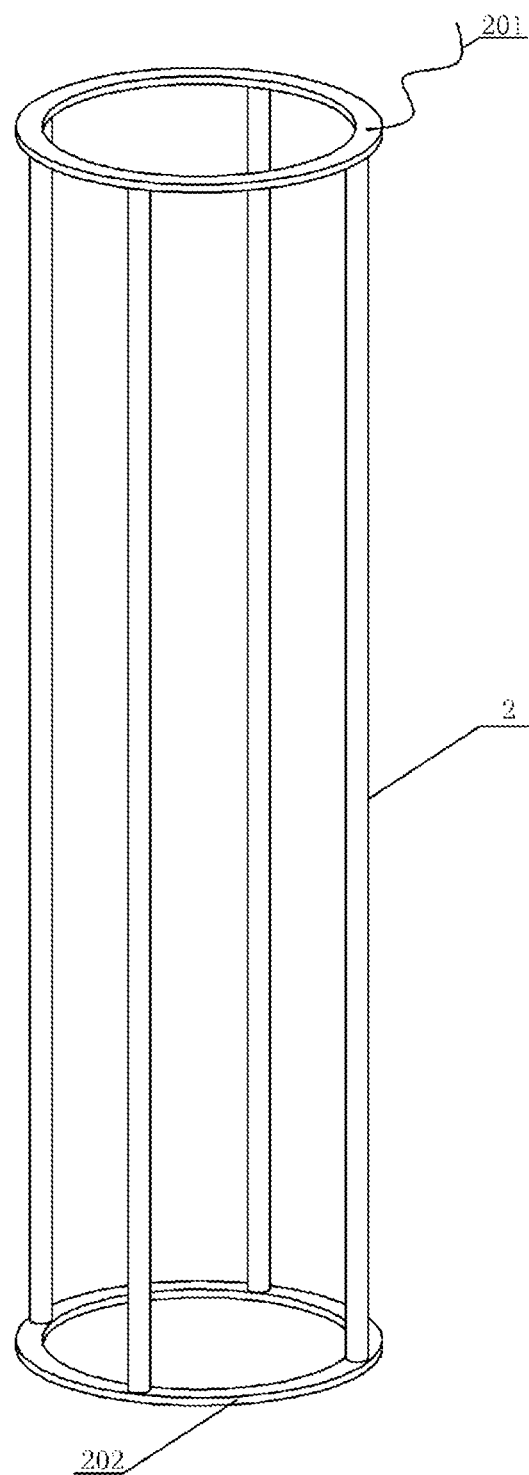
FIG. 2 is a schematic view of a second electrode according to the present invention.
Figure 3:
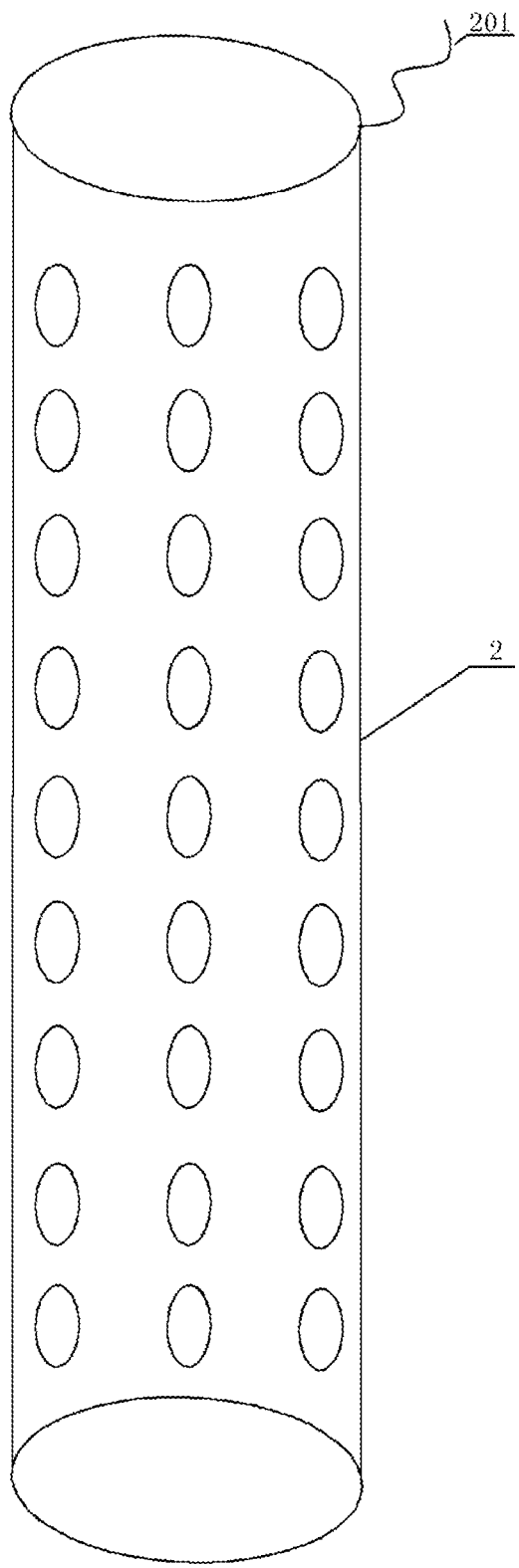
FIG. 3 is another schematic view of the second electrode according to the present invention.

The second electrode 2 provided in the present invention may be, as shown in FIG. 2, formed by at least one tubular or rod-shaped conductor connected in parallel, and the conductors have a same transverse structure and are connected in parallel with the first electrode in the vertical direction. The tubular or rod-shaped conductors 2 are connected together through a connector 202. In the horizontal direction, the first electrode is partially or completely surrounded by the second electrode. Alternatively, as shown in FIG. 3, the second electrode is a cylindrical structure which provided with uniform distributed holes. According to the holes provided, the structures and areas of the portions of the second electrode corresponding to the segment electrodes on the first electrode are approximately same can be ensured. The second electrode 2 is generally electrically connected to the signal and data processing 5 via a second electrode lead 201.

The second electrode formed by the tubular or rod-shaped electrodes connected in parallel has the following advantages: it is easy to process the surface of the tubular or rod-shaped electrode to be more smooth; moreover, in the vertical direction of the measuring area, it can be ensured that there is no protruding point blocking the movement of the medium on the tubular or rod-shaped electrodes, thereby minimizing the influence of the hanging, it is significant in measurement of the crude oil emulsion with a higher viscosity.

Figure 4:
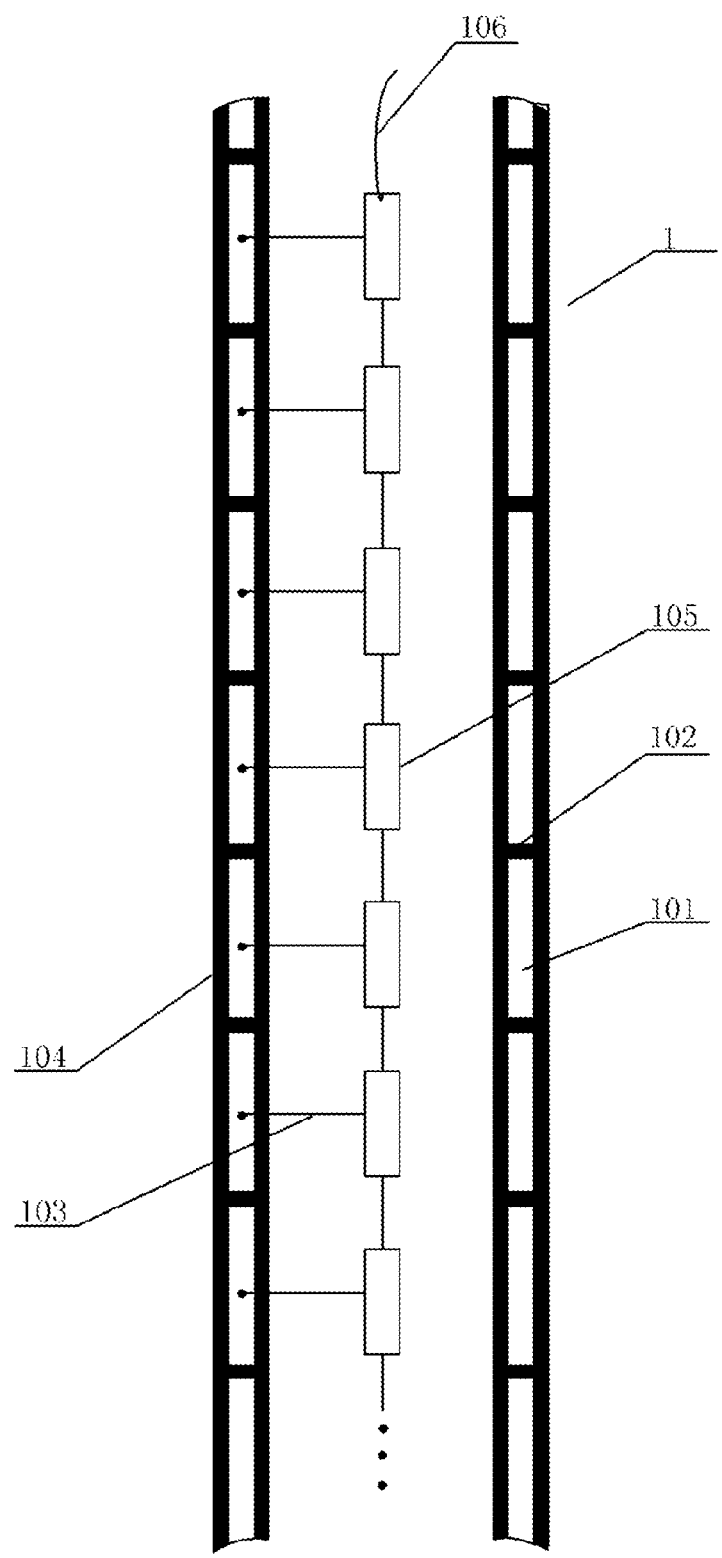
FIG. 4 is a schematic view of another composition structure of a first electrode according to the present invention.

In a technical solution according to the present invention, the segment sensors may share one or more segment signal measuring circuits 502. The one or more shared segment signal measuring circuits 502 are electrically connected to the signal and data processing unit 5, and are electrically connected to the segment electrode 101 through an electronic switch 501, as shown in FIG. 1. Each of the segment sensors may configure its own segment signal measuring circuit 105, and after an A/D conversion, each of the segment sensors is electrically connected to the signal and data processing unit 5 via a serial or parallel data transfer bus 106, as shown in FIG. 4.

When determining the segment signal measurement circuit 105 is a capacitance measuring circuit or an impedance measuring circuit, and a connection mode among the segment signal measurement circuit 105 and the data processing unit 5, segment electrode 101 and the like, it is clear to those skilled in the art that, in addition to taking account into whether the process is simple and reliable, it is required to reduce the effect of the parasitic parameters.

An embodiment of the present invention will be described below, the above electrode structure or the probe is served as an oil-water composition measuring apparatus probe for measuring the water content or oil content. Firstly, produced fluid of oil well is inputted into a vertical separation tank through an input line. After the gas and liquid in the fluid are separated in the separation tank, a gas layer is formed on the upper part of the separation tank. After the gas is discharged via a gas output line located on the upper part of the separation tank, and the liquid drain valve is closed, the liquid is concentrated in the separation tank; according to the settling separating characteristics of the liquid, an emulsified oil layer is formed in the middle of the separation tank and a free water layer is formed on the lower part. The liquid level in the tank is measured by a liquid level indicator provided on the separation tank. Once the liquid level is reached the required height, the produced fluid of oil well input time T is record. Several oil-water composition measuring apparatus probes are mounted at the different preset heights of the separation tank in the vertical direction. Each of the probes measures the oil content $\eta_i$ of the liquid level layer on which the probe is located. An intermediate horizontal level of two adjacent probes is set as an upper interface or lower interface of one liquid level layer. The thickness $h_i$ and horizontal cross-sectional area $S_i$ of the liquid level layer on which each probe is located are determined, depending on the structure size of the separation tank and installation settings of the probe. The oil content volume $V_{i\ oil}$ of the liquid level layer on which each probe is located is calculated, then plus the oil content volumes $V_{i\ oil}$ of the liquid layers on which each probe is located, work out oil production volume $V_{oil}$ of the oil well within the inlet liquid time T.

The water content measuring technique of the present invention is specifically described as follows. A vertical separation tank is inputted by produced fluid of oil well through an input line. After the gas and liquid in the fluid are separated in the separation tank, a gas layer is formed on the upper part of the separation tank. After the gas is discharged via a gas output line located on the upper part of the separation tank, and the liquid drain valve is closed, and the liquid is concentrated in the separation tank; according to the settling separating characteristics of the liquid, an emulsified oil layer is formed in the middle of the separation tank and a free water layer is formed on the lower part. A liquid level indicator is provided on the separation tank for measuring the liquid level in the tank. Several oil-water composition measuring apparatus probes are provided at the different preset heights of the separation tank in the vertical direction. Each oil-water composition measuring apparatus probe completely immersed by the liquid positions a horizontal liquid layer in the vertical direction, in which the oil-water composition measuring apparatus probe is contained, the oil content $\eta_i$ of the horizontal liquid layer can be represented by the data measured by the oil-water composition measuring apparatus probe and the horizontal liquid layer has a certain thickness $h_i$. The adjacent horizontal liquid level layers are seamless docked with each other. The upper liquid level of a horizontal liquid level layer is defined depending on the heights and the measuring ranges of the oil-water composition measuring apparatus probe contained in the horizontal liquid level layer and its adjacent upper and probe in the vertical direction; the lower liquid level of the horizontal liquid level layer is defined depending on the heights and the measuring ranges of the oil-water composition measuring apparatus probe contained in the horizontal liquid level layer and its adjacent lower probe. The height difference of a horizontal liquid level layer between the upper liquid level and the lower liquid lever is the thickness $h_i$ of the horizontal liquid level layer. In the ideal case, in the vertical direction, the ranges measured by the each oil-water composition measuring apparatus probes are the same, and the distances between the adjacent two oil-water composition measuring apparatus probes are the same. Therefore, the thickness $h_i$ of each horizontal liquid level layer is the height difference between center points of two adjacent probes. The vertical distance between the adjacent oil-water composition measuring apparatus probes should be as smaller as possible to improve the accuracy of oil-water measurement. Several oil-water composition measuring apparatus probes in the vertical direction are distributed in the emulsified oil layer located in the middle of the separation tank, and downwardly extends into the free water level and upwardly extends into the gas layer.

Once the liquid level indicator monitors that the liquid level in the separation tank is reached the required height, recording data is immediately started; or when the produced liquid of oil well is transported to the short pipeline through a valve, recording data is started, these data include an inlet liquid time T, the total height of the liquid level H, oil content $\eta_i$ of each horizontal liquid level layer and the like. Since the structure size of the separation tank is known, after obtaining the total height of the liquid level H, the volume of the liquid V produced by an oil well within the inlet liquid time T can be obtained. For each horizontal liquid level layer i positioned by the oil-water composition measuring apparatus probe, from the lowermost horizontal liquid level layer of which the $\eta_i$ is zero to the first complete horizontal liquid level layer n under the liquid level, the oil content rate $\eta_i$, thickness $h_i$, and the horizontal cross-sectional area $S_i$ of each of the horizontal liquid level layer are known; however, there is an incomplete horizontal liquid level layer n+1 between the total liquid level and the first complete horizontal liquid level layer, its height is equal to the total height of the liquid level H minus the upper liquid level height $H_{n\ upper}$ of the layer n, and its liquid oil content approximates to the oil content of the layer n. Thereby, the oil content volume $V_{ioil}$ of each complete horizontal liquid level layer and the oil content volume $V_{n+1oil}$ of the incomplete horizontal liquid level layer on the uppermost can be obtained by calculating, and the volume $V_{oil}$ of the oil produce by the oil well within the inlet liquid time T can be obtained by summing the oil content volume of all horizontal liquid level layers above.

$$V_{oil} = \sum_{n_i=0}^{\eta_n} S_i h_i \eta_i + S_{n+1} \eta_n (H - H_{nupper})$$

In this way, not only the liquid production of the oil well within a preset time can be measured, but also the corresponding oil production can be measured.

After this measurement, the exhaust valve is closed, the liquid drain valve and liquid inlet valve are opened. After the liquid in the separation tank is emptied, the next measurement can be performed.

The apparatus of the present invention will be further described in conjunction with accompanying drawings and embodiments below.

Figure 5:
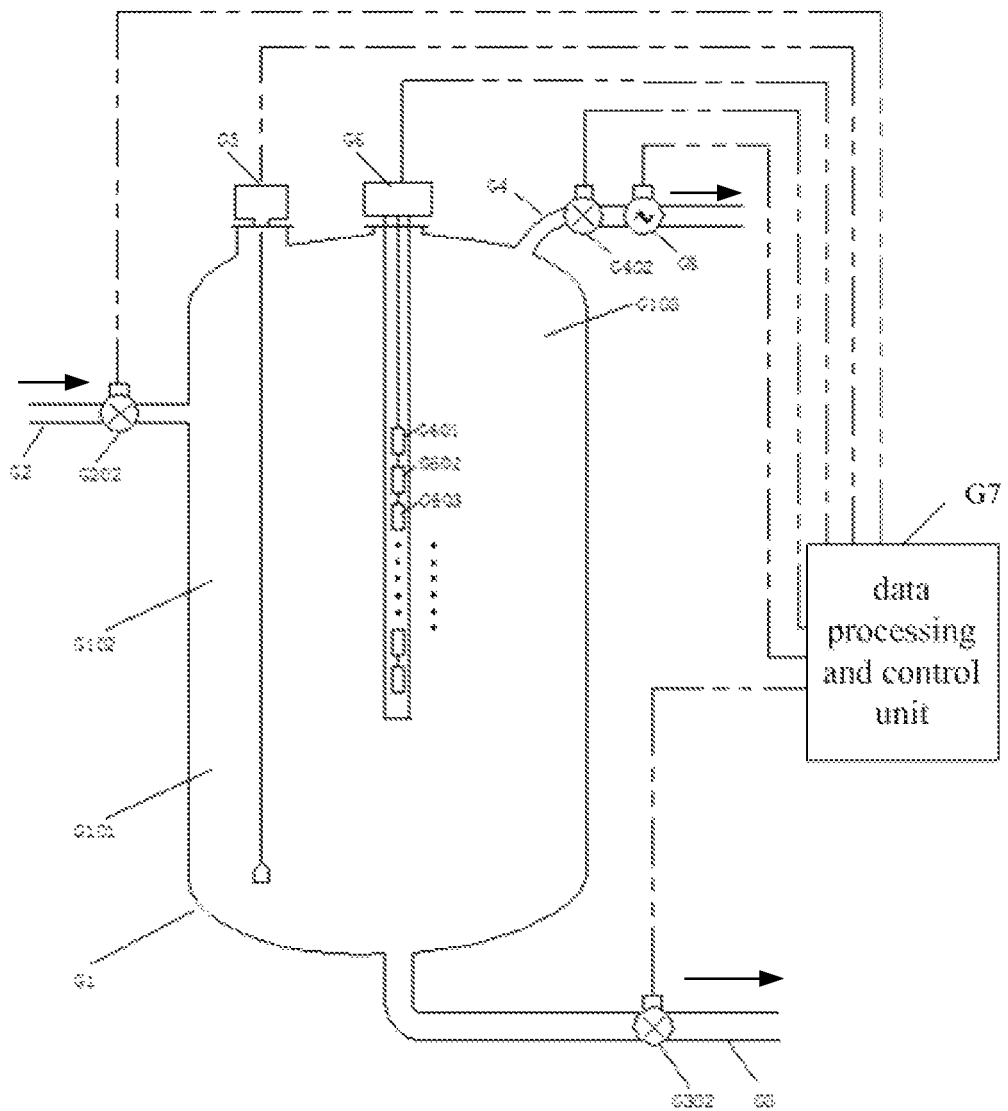
FIG. 5 is a schematic view of an apparatus for measuring water content according to a first embodiment of the present invention.

Embodiment 1: as shown in FIG. 5, an apparatus for measuring oil content of produced liquid of oil well is provided with a vertical separation tank G1. A produced liquid of oil well input pipeline G2, a liquid output pipeline G3 and a gas output pipeline G4 are provided on the upper portion, lower portion, and top portion of the separation tank G1, respectively. A liquid inlet valve G202 is provided on the produced liquid of oil well input pipeline G2, a liquid drain valve G302 is provided on the liquid output pipeline G3, and an exhaust valve G402 is provided on the gas output pipeline G4. A liquid level indicator G5 for monitoring the liquid level is further provided on the separation tank. In particular, an oil-water composition measuring apparatus G6 composed of several oil-water composition measuring apparatus probes is provided on the separation tank G1, that is, the above electrode structure, which can measure the oil content or water content of the horizontal liquid level layers on which the probes are located. An oil-water composition measuring apparatus G6 is mounted on top of the separation tank G1. In the vertical direction, for each oil-water constituents measuring instrument probe such as G601, G602 and the like, their position are confirmed, and the liquid layer represented by the data measured by two adjacent oil-water composition measuring apparatus probes abut against each other.

The oil-water composition measuring apparatus probes, such as G601, G602 and the like, which compose the oil-water composition measuring apparatus G6. Each of the probes independently completes the oil content measurement of the horizontal liquid layer on which the probe is located i, and the measured oil content represents the average oil content of the horizontal liquid level layer.

The liquid layers represented by the data obtained by two adjacent oil-water composition measuring apparatus probe abuts against each other. For example, the lower interface of the liquid layer in which G601 is located is the upper interface of the liquid layer in which G602 is located. The lower interface of the oil layer in which G602 is located is the upper interface of the oil layer in which G603 is located.

Each of the oil-water composition measuring apparatus probes may connect one corresponding data processing and display module, or one data processing and display module may be shared by multiple oil-water composition measuring apparatus probes, which is known by the person skilled in the art.

Figure 6:
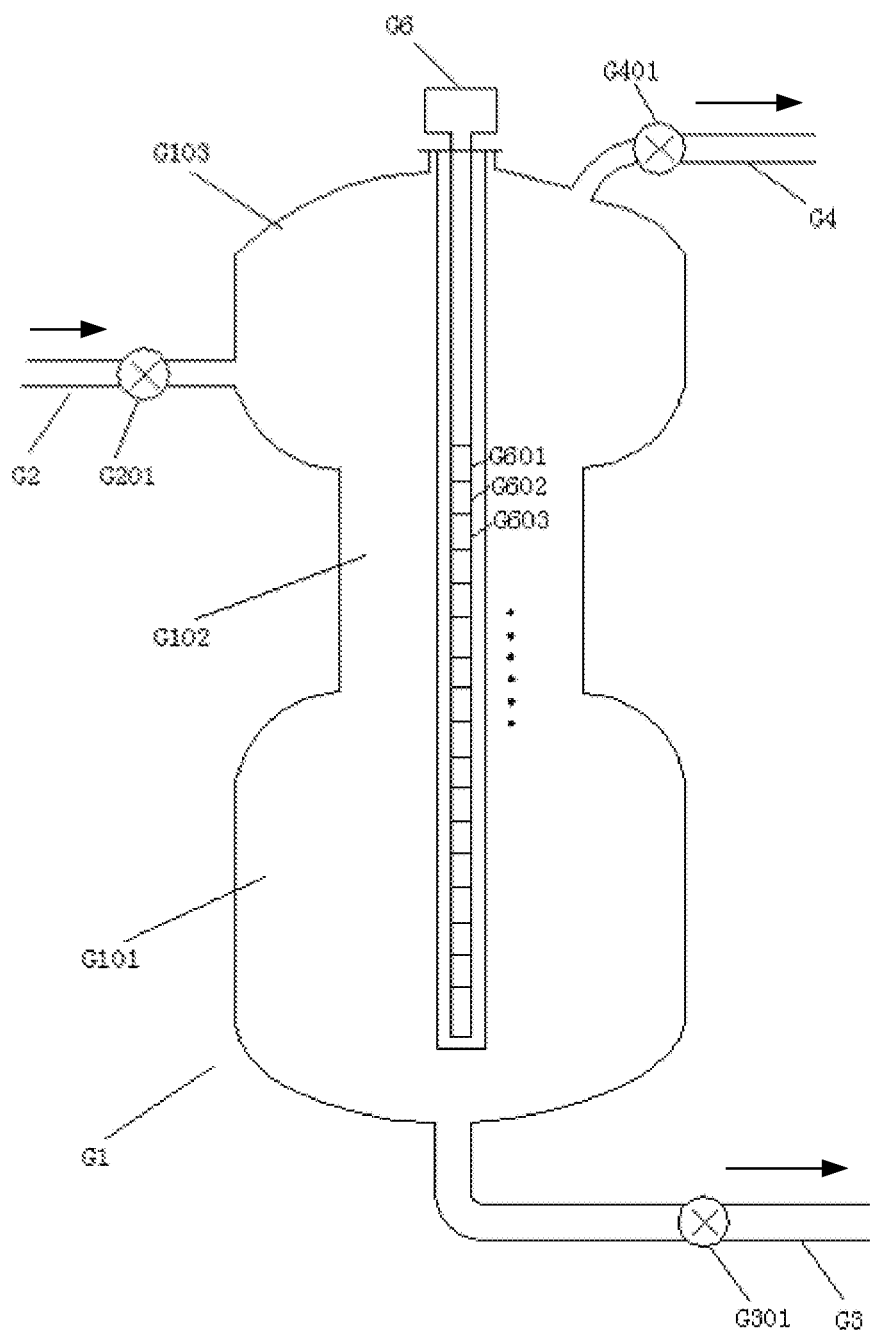
FIG. 6 is a schematic view of an apparatus for measuring water content according to a second embodiment of the present invention.

Embodiment 2: as shown in FIGS. 5 and 6, an apparatus for measuring oil content of produced liquid of oil well includes oil-water composition measuring apparatus probes G601, G602, G603 . . . etc. In the case that the distance between the adjacent probes is small enough, the oil-water composition measuring apparatus stated above can not only measure the oil-water compositions of each liquid layer, but also can serve as a liquid level indicator.

Embodiment 3: FIG. 6 shows an apparatus for measuring oil content of produced liquid of oil well. Herein, the transverse section of the water collecting bin G101 at the bottom of the separation tank and the transverse section of the oil collecting bin G102 in the middle of the separation tank are circular, the diameter of the transverse section of the oil collecting bin G102 is one half of that of the water collecting bin G101, the height of the oil collecting bin G102 is third-fifths of that of the water collecting bin G101, and other features are the same as the embodiment 2. According to the approximate ratio of the oil-water of the produced liquid of oil well, the transverse section and the height of the oil collecting bin and the transverse section and the height of the water collecting bin can be adjusted. Obviously, in the case that the oil content is low, the smaller the transverse section of the oil collecting bin is and the greater the height of the oil collecting bin is, the accuracy of measuring the oil content is higher.

Embodiment 4: FIG. 6 shows an apparatus for measuring oil content of produced liquid of oil well. Herein, the transverse section of the water collecting bin G101 at the bottom portion of the separation tank and the transverse section of the oil collecting bin G102 in the middle portion of the separation tank are circular, the diameter of the transverse section of the oil collecting bin G102 is one third of that of the water collecting bin G101, other features are the same as the embodiment 3.

Embodiment 5: FIG. 6 shows an apparatus for measuring oil content of produced liquid of oil well. Herein, a data processing and control unit G7 is provided, and is electrically connected to an electric liquid inlet valve G202, an electric liquid drain valve G302, an electric exhaust valve G402 that are located on the pipelines, a liquid level indicator 5, each oil-water composition measuring apparatus probe G601, G602, G603 . . . , and a gas flow indicator G8. The data processing and control unit 7 controls the operation of each electric valve, and perform fast processes on the data collected to timely output the metering result of the measured oil well. Other features are the same as the embodiment 1.

Additional note 1: an integrated apparatus for measuring water content, including: a signal and data processing unit, a supporting and connecting body, and a sensor extending into a container and contacting to multiphase medium. Herein, the sensor is composed of a first electrode and a second electrode, and the first electrode and the second electrode are fixed and connected via a supporting and connecting body respectively. In particular:

the first electrode is composed of a group of tubular conductive segment electrodes in the vertical direction, the segment electrodes are fixed and insulated to each other via an insulating material, and are electrically connected to the signal and data processing unit through a lead located inside the segment electrode; an insulating layer is uniformly wrapped on the first electrode;

the second electrode is located along with the first electrode in the vertical direction and is electrically connected to the signal and data processing unit. The second electrode and the first electrode are parallel to each other in the vertical direction, they are spaced and insulated from each other via an isolating and insulating part in the horizontal direction, the space between the second electrode and the first electrode is a measuring space of the sensor.

2. The integrated apparatus for measuring water content according to additional note 1, herein: the second electrode is formed by several conductive tubular or rod-shaped electrodes in parallel.

3. The integrated apparatus for measuring water content according to additional note 1, herein: the second electrode has a conductive cylindrical structure, and the lateral surface of the cylindrical structure is provided with holes distributed uniformly along a horizontal direction and a vertical direction.

4. The integrated apparatus for measuring water content according to additional note 1, herein: the space between the first electrode and the second electrode is smaller than the height of the segment electrode of the first electrode, the range length of the space between the first electrode and the second electrode ranges from 5 mm to 300 mm, the height of the segment electrode of the first electrode ranges from 10 mm to 400 mm.

5. The integrated apparatus for measuring water content according to additional note 1, herein: the thickness of the insulating layer wrapped on the first electrode is less than 1.5 mm.

6. The integrated apparatus for measuring water content according to note 1, herein: the relative dielectric coefficient of material of the insulating layer wrapped on the first electrode ranges from 3 to 2000.

7. The integrated apparatus for measuring water content according to note 1, herein: the insulating layer wrapped on the first electrode is a ceramic tube, a rubber tube or a plastic tube, and the insulating layer is tightly sleeved on the outside of the first electrode.

8. The integrated apparatus for measuring water content according to note 1, herein: the insulating layer wrapped on the first electrode is a fluorine plastic film, and is tightly attached to the outside of the first electrode by injection moulding or spraying curing.

The above detailed description of the invention is not exhaustive, the invention should not be limited to the precise forms disclosed above. It will become understood to one skilled in the art, within the scope of the invention, various equivalent modifications and alterations can be made, such modifications and alterations should be deemed to be covered by the invention. Elements of each embodiment described above can be arbitrarily combined together in order to provide further implementation technical solution. In addition, the term used in the appended claims should not be interpreted or the invention should not be limited to the specific embodiment disclosed in the specification, unless this term is clearly defined by the above details. Accordingly, the embodiment and all equivalents implemented according to claims should be covered by the actual scope of the invention.

What is claimed is:

1. An electrode structure for measuring water content, comprising a first electrode and a second electrode, wherein an insulating layer is wrapped around the first electrode, and the first electrode and the second electrode are fixed and connected to each other via a supporting and connecting body insulatively, wherein:

the first electrode comprises a plurality of tubular conductive segment electrodes arranged along a first direction, every two adjacent segment electrodes are insulated from each other, a first space is formed between the two adjacent segment electrodes, the two adjacent segment electrodes are operatively electrically connected to a signal and data processing unit; the second electrode is arranged around the first electrode and extends along the first direction, and is operatively electrically connected to the signal and data processing unit;

a second space is formed between the first electrode and the second electrode in a second direction perpendicular to the first direction;

the second electrode comprises one or more parallel rod-shaped electrodes, a third space is formed between the rod-shaped electrodes; or the second electrode comprises a conductive cylindrical structure extending along the first direction, and a lateral surface of the cylindrical structure is provided with holes distributed uniformly along a horizontal direction and a vertical direction;

wherein a length of the second space is smaller than a height of the segment electrode of the first electrode.

2. The electrode structure according to claim 1, wherein the rod-shaped electrodes are operatively electrically connected in parallel.

3. The electrode structure according to claim 1, wherein viewed from a cross-section perpendicular to the first direction, the parallel rod-shaped electrodes of the second electrode are arranged along a circumference of a circle, and the first electrode is arranged on a center of the circle.

4. The electrode structure according to claim 1, wherein a length of the first space is smaller than a height of one of its adjacent segment electrodes.

5. The electrode structure according to claim 1, wherein lengths of the third spaces are approximately the same.

6. The electrode structure according to claim 1, wherein a length of the second space ranges from 5 mm to 300 mm, and the height of the segment electrode of the first electrode ranges from 10 mm to 400 mm.

7. The electrode structure according to claim 1, wherein a thickness of the insulating layer wrapped on the first electrode is less than 3 mm.

8. The electrode structure according to claim 1, wherein a relative dielectric coefficient of material of the insulating layer wrapped on the first electrode ranges from 2 to 2000.

9. The electrode structure according to claim 1, wherein the insulating layer wrapped on the first electrode is a ceramic tube, a rubber tube or a plastic tube, and the insulating layer is tightly sleeved on the first electrode.

10. The electrode structure according to claim 1, wherein the insulating layer wrapped on the first electrode is a fluorine plastic film, and is tightly attached on the first electrode by injection moulding or spraying curing.

11. An integrated apparatus for measuring water content, comprising:

a tank, arranged vertically for accommodating a multiphase medium; and the electrode structure according to claim 1, wherein the electrode structure is arranged in the tank, and the first direction of the electrode structure is a vertical direction.

12. The integrated apparatus for measuring water content according to claim 11, wherein the tank comprises a separation tank, and the separation tank comprises:

an upper portion with a first height and a first transverse section;

a middle portion with a second height and a second transverse section; and a lower portion with a third height and a third transverse section;

wherein a ratio between the second height of the middle portion and the third height of the lower portion, and a ratio between an area of the second transverse section of the middle portion and an area of the third transverse section of the lower portion are configured according to an approximate ratio between a volume of water and a volume of oil of the multiphase medium.

13. The integrated apparatus for measuring water content according to claim 12, wherein the area of the second transverse section of the middle portion is smaller than the area of the third transverse section of the lower portion.

14. The integrated apparatus for measuring water content according to claim 12, wherein the area of the second transverse section of the middle portion is smaller than an area of the first transverse section of the upper portion.

15. The integrated apparatus for measuring water content according to claim 12, wherein the transverse section is circular.

* * * * *